United States Patent
Kobayashi et al.

(10) Patent No.: US 8,349,882 B2
(45) Date of Patent: Jan. 8, 2013

(54) PHARMACEUTICAL COMPOSITION FOR EXTERNAL USE

(75) Inventors: Hirokazu Kobayashi, Yokohama (JP); Akira Nozawa, Yokohama (JP); Katsumasa Ariyoshi, Yokohama (JP)

(73) Assignees: Nihon Nohyaku Co., Ltd., Chuo-ku, Tokyo (JP); Pola Pharma Inc., Shinagawa-ku, Tokyo (JP)

( * ) Notice: Subject to any disclaimer, the term of this patent is extended or adjusted under 35 U.S.C. 154(b) by 206 days.

(21) Appl. No.: 12/281,967

(22) PCT Filed: Oct. 2, 2006

(86) PCT No.: PCT/JP2006/319708
§ 371 (c)(1),
(2), (4) Date: Sep. 5, 2008

(87) PCT Pub. No.: WO2007/102242
PCT Pub. Date: Sep. 13, 2007

(65) Prior Publication Data
US 2009/0137651 A1    May 28, 2009

(30) Foreign Application Priority Data

Mar. 8, 2006 (JP) .................................. 2006-062079
Aug. 8, 2006 (JP) .................................. 2006-215871

(51) Int. Cl.
*A61K 31/4178* (2006.01)
*A61Q 3/00* (2006.01)
*A01P 3/00* (2006.01)

(52) U.S. Cl. ...................... 514/397; 424/61; 424/400
(58) Field of Classification Search .............. 514/397; 424/61, 400
See application file for complete search history.

(56) References Cited

U.S. PATENT DOCUMENTS

| | | | |
|---|---|---|---|
| 4,267,169 A | 5/1981 | Kamishita et al. | |
| 4,636,520 A | 1/1987 | Umio et al. | |
| 4,764,381 A | 8/1988 | Bodor et al. | |
| 5,340,836 A | 8/1994 | Reinhard et al. | |
| 5,690,923 A | 11/1997 | De Vringer et al. | |
| 5,753,256 A * | 5/1998 | Cordes et al. .................. 424/443 |
| 5,814,305 A | 9/1998 | Laugier et al. | |
| 5,962,536 A | 10/1999 | Komer | |
| 5,993,787 A | 11/1999 | Sun et al. | |
| 6,007,791 A | 12/1999 | Coombes et al. | |
| 6,008,256 A | 12/1999 | Haraguchi et al. | |
| 6,017,920 A | 1/2000 | Kamishita et al. | |
| 6,083,518 A | 7/2000 | Lindahl | |
| 6,428,654 B1 | 8/2002 | Cronan, Jr. et al. | |
| 6,585,963 B1 | 7/2003 | Quan et al. | |
| 6,740,326 B1 | 5/2004 | Meyer et al. | |
| 2003/0017207 A1 | 1/2003 | Lin et al. | |
| 2003/0235541 A1 | 12/2003 | Maibach et al. | |
| 2004/0208906 A1 | 10/2004 | Tatara et al. | |
| 2005/0232879 A1 | 10/2005 | Sasagawa et al. | |
| 2006/0140984 A1 | 6/2006 | Tamarkin et al. | |
| 2007/0099932 A1 | 5/2007 | Shirouzu et al. | |
| 2008/0031835 A1 | 2/2008 | Kawamura et al. | |
| 2009/0030059 A1 | 1/2009 | Miki et al. | |
| 2009/0076109 A1 | 3/2009 | Miki et al. | |
| 2009/0099202 A1 | 4/2009 | Shirouzu et al. | |
| 2009/0137651 A1 | 5/2009 | Kobayashi et al. | |
| 2009/0202602 A1 * | 8/2009 | Ishima et al. .................. 424/405 |
| 2010/0168200 A1 | 7/2010 | Masuda et al. | |
| 2010/0173965 A1 | 7/2010 | Masuda et al. | |
| 2010/0204293 A1 | 8/2010 | Masuda et al. | |
| 2010/0210702 A1 | 8/2010 | Vontz et al. | |
| 2010/0210703 A1 | 8/2010 | Vontz et al. | |
| 2012/0014893 A1 | 1/2012 | Kobayashi et al. | |
| 2012/0022120 A1 | 1/2012 | Kobayashi et al. | |

FOREIGN PATENT DOCUMENTS

| EP | 0 070 525 | 1/1983 |
|---|---|---|
| EP | 0 440 298 | 8/1991 |
| EP | 0 715 856 | 6/1996 |
| EP | 1 138 314 | 10/2001 |
| EP | 1 522 316 | 4/2005 |
| EP | 1 537 868 | 6/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |

(Continued)

OTHER PUBLICATIONS

Derwent Abs of WO/2007077806 A1, Jul. 2007, Japan, Ishima, T, et al., A 61 K 47/22.*
Uchida et al. (J.Infect. Chemother., vol. 10, 2004, pp. 216-219.*
JP 2005-289879, English translation of the patent, dated Oct. 2005, Translated on the internet on Aug. 19, 2010.*
Examination Report issued Apr. 8, 2010 to corresponding New Zealand Patent Application No. 571818.

(Continued)

*Primary Examiner* — Savitha Rao
(74) *Attorney, Agent, or Firm* — Knobbe, Martens, Olson & Bear, LLP

(57) ABSTRACT

A pharmaceutical composition for external use, including: i) luliconazole represented by the following structural formula (1) and/or a salt thereof; and ii) one or two or more selected from N-methyl-2-pyrrolidone, propylene carbonate, and crotamiton.

Structural formula (1)

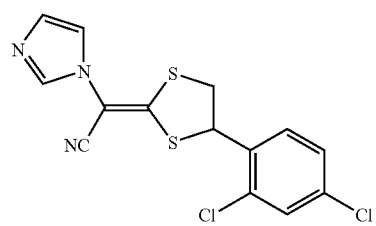

20 Claims, No Drawings

FOREIGN PATENT DOCUMENTS

| | | |
|---|---|---|
| JP | 61-118315 | 6/1986 |
| JP | 62-093227 | 4/1987 |
| JP | 62-223163 | 10/1987 |
| JP | 01-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 07-74144 | 8/1995 |
| JP | 07-206711 | 8/1995 |
| JP | 07-223971 | 8/1995 |
| JP | 08-020527 | 1/1996 |
| JP | 10-152433 | 6/1998 |
| JP | 10-226639 | 8/1998 |
| JP | 10-226686 | 8/1998 |
| JP | 2001-064206 | 3/2001 |
| JP | 2002-114680 | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-154306 | 6/2005 |
| JP | 2005-239678 | 9/2005 |
| JP | 2005-289879 | 10/2005 |
| JP | 2005289879 * | 10/2005 |
| JP | 2006-028123 | 2/2006 |
| JP | 2006-306734 | 11/2006 |
| RU | 2 270 894 C2 | 3/2004 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2004/091521 | 10/2004 |
| WO | WO 2005/099764 | 10/2005 |
| WO | WO 2005/123136 | 12/2005 |
| WO | WO 2006/038317 | 4/2006 |
| WO | WO 2007/077806 | 7/2007 |
| WO | WO 2007/102242 | 9/2007 |
| WO | WO 2007/077806 * | 12/2007 |
| WO | WO 2008/075207 | 6/2008 |
| WO | WO 2010/093992 | 8/2010 |

OTHER PUBLICATIONS

GHS Classification Guidance for Enterprises (2$^{nd}$ Edition, Ministry of Economy, Trade and Industry, Japan, Mar. 2010.
Crotamiton Properties (http://www.chemspider.com/Chemical-Structure.2780.html) 2 pages.
Absolute ethanol MSDS (www.sciencelab.com/msds.php?msdsld=9923955) 7 pages.
Methyl Ethyl Ketone MSDS (www.sciencelab.com/msds.php?msdsld=9927358) 6 pages.
Niwano, et al. "Lanoconazole and Its Related Optically Active Compound NND-502: Novel Antifungal Imidazoles with a Ketene Dithioacetal Structure," *Current Medicinal Chemistry*, vol. 2, pp. 147-160, 2003.
Martins, et al. "In vitro Sensitivity of Dermatophytes to Urea," *Clinics*, vol. 61, No. 1, pp. 9-14, 2006.
Uchida, et al. "In vitro Antifungal Activity of Luliconazole (NND-502), a Novel Imidazole Antifungal Agent," *Journal of Infectious Chemotherapy*, vol. 10, pp. 216-219, 2004.
TransPerfect translation of JP 2005-289879.
Niwano, et al. "In Vitro and in Vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.
Vieira, et al. "Cationic Lipids and Surfactants as Antifungal Agents: Mode of Action," *Journal of Antimicrobial Chemotherapy*, Vo. 58, pp. 760-767, 2006.
SDS Density downloaded from www.chemicalbook.com/ChemicalProductProperty_EN_CB2147453.htm 2 pages, copyright 2010.
Pluronics Density downloaded from www.chemicalbook.com/ChemicalProductPropertyEN_Cb2709101.htm 2 pages, copyright 2010.
Ethyl Cellulose Density downloaded from www.chemicalbook.com/ProductMSDSDetailCB6165620_EN.htm 3 pages, copyright 2008.
Niwano, et al. "Efficacy of NND-502, a Novel Imidazole Antimycotic Agent, in Experimental Models of *Candida albicans* and *Aspergillus fumigatus* Infections," *International Journal of Antimicrobial Agents*, vol. 12, pp. 221-228, 1999.
Uchida, et al. "In vitro Activity of Novel Imidazole Antifungal Agent NND-502 Against *Malassezia* Species," *International Journal of Antimicrobial Agents*, vol. 21, pp. 234-238, 2003.
Supplemental European Search Report dated Aug. 16, 2010, issued to corresponding European patent application 06811056.8.
Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.
Office action issued to corresponding Israeli Patent Application No. 193894 on Oct. 14, 2010 with translation.

* cited by examiner

PHARMACEUTICAL COMPOSITION FOR EXTERNAL USE

CROSS-REFERENCE TO RELATED APPLICATIONS

This application is the U.S. National Phase under 35 U.S.C. §371 of International Application PCT/JP2006/319708, filed Oct. 2, 2006, which was published in a non-English language, which claims priority to JP Patent Application No. 2006-062079, filed Mar. 8, 2006 and JP Patent Application No. 2006-215871 filed Aug. 8, 2006.

TECHNICAL FIELD

The present invention relates to a pharmaceutical composition for external use, and more particularly, to a pharmaceutical composition for external use, which can be preserved in a state where a decrease in optical purity is suppressed.

BACKGROUND ART

The Japanese archipelago extends from a subtropical zone to a temperate zone and has a warm climate high in humidity, which is liable to facilitate propagation of fungi such as molds. In addition, due to westernization of clothes, people are now accustomed to wearing shoes on feet. Accordingly, a foot serves as a favorable environment for the propagation of the fungi, leading to mycotic skin diseases that are serious social issues nowadays. Of those, onychomycosis has a low complete cure rate and high relapsing and reinfection rates. Therefore, an effective therapy has been demanded.

Conventionally, treatments mainly using tolnaftate formulations have been conducted on such diseases. In recent years, imidazole-based antifungal agents, such as bifonazole and itraconazole, are mainly used.

As the imidazole-based antifungal agents, there are commercially available imidazole-based antifungal agents such as those represented by the general formula (1) described below, specifically, luliconazole represented by the structural formula (1) below and lanoconazole represented by the structural formula (2) below. A commercially available product called "Lulicon" (registered trademark) is also present (e.g., see Patent Document 1 and Patent Document 2).

The luliconazole is an imidazole-based antifungal agent having optical activity with a wide antifungal spectrum, in particular, shows remarkable antifungal activity against dermatophytes. In addition, the luliconazole is also characterized in that its retention in the stratum corneum is extremely high, and thus is a compound expected to be applied to treatment of onychomycosis. Like other imidazole-based antifungal agents, however, luliconazole and lanoconazole are agents having problems in their solubility, so there is a need of using a solvent for their preparation. On the other hand, in some cases, the characteristic features of luliconazole may include a risk of a decrease in its optical purity when it is stored in a dissolved state under severe circumstances due to a type of a solvent used for dissolution, temperature, acid and base, or the like. Besides, such a decrease in optical purity may relate to a solvent. In other words, with regard to a pharmaceutical composition for external use containing luliconazole and/or a salt thereof, it is desirable to provide means for increasing the solubility thereof while suppressing a decrease in optical purity even under severe environment.

A decrease in optical purity is a common phenomenon, which sometimes occurs in an optically active compound according to storage conditions, particularly under severe conditions at high temperature. However, no means for suppressing the phenomenon is known.

Heretofore, in a pharmaceutical technology for antifungal agents, various studies have been conducted for increasing the solubility thereof (see, for example, Patent Documents 3 to 5). However, the antifungal agents to be dissolved show increases different in their solubility. Therefore, the effect of one of them cannot be directly applied to the other compounds. Among the solvents, a solvent that acts to prevent the optically active compound from a decrease in optical purity has not yet been known.

On the other hand, as a pharmaceutical preparation containing luliconazole and/or a salt thereof, a pharmaceutical preparation containing a film-forming agent and a polyoxypropylene/polyoxyethylene copolymer has been known (see, for example, Patent Document 6), but one containing N-methyl-2-pyrrolidone, propylene carbonate, or crotamiton has not been known at all. In addition, a basic process for manufacturing an imidazole-based compound is also already known in the art (see, for example, Patent Document 7):

[Chem 1]

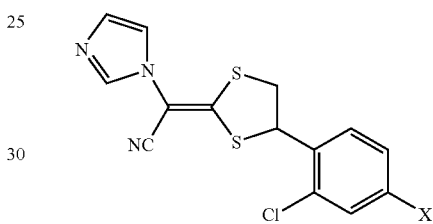

General formula (1)

where X represents a hydrogen atom or a chloride atom.

[Chem 2]

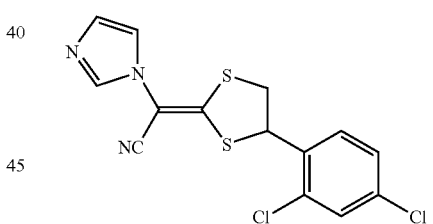

Structural formula (1)

[Chem 3]

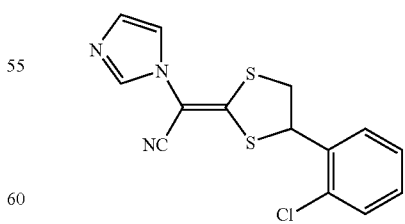

Structural formula (2)

Patent Document 1: JP 10-226686 A
Patent Document 2: JP 2-275877 A
Patent Document 3: JP 5-306223 A
Patent Document 4: JP 7-206711 A
Patent Document 5: WO96/11710

Patent Document 6: WO03/105841
Patent Document 7: JP 62-93227 A

DISCLOSURE OF THE INVENTION

Problem to be Solved by the Invention

The present invent has been made under such circumstances, and an object of the present invention is to provide a technique of dissolving luliconazole and/or a salt thereof (hereinafter, also referred to as "luliconazole or the like") and preserving the luliconazole or the like in a state where a decrease in optical purity is suppressed.

Means for Solving the Problem

In consideration of such a situation, the inventors of the present invention have made intensive studies and efforts to obtain a technique of dissolving luliconazole and/or a salt thereof and preserving the luliconazole or the like in a state where a decrease in optical purity is suppressed and have finally completed the present invention by finding out that the luliconazole or the like can be stored in a state where a decrease in optical purity thereof is suppressed in addition to increase the solubility of the luliconazole or the like by dissolving the luliconazole or the like in an organic solvent, such as N-methyl-2-pyrrolidone, propylene carbonate, or crotamiton. In other words, the present invention is as follows:

(1) A pharmaceutical composition for external use, including: i) luliconazole represented by the following structural formula (1) and/or a salt thereof; and ii) one or two or more selected from N-methyl-2-pyrrolidone, propylene carbonate, and crotamiton.

[Chem 4]

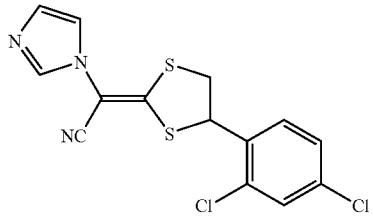

Structural formula (1)

(2) A pharmaceutical composition for external use according to the item (1), in which the pharmaceutical composition for external use is provided for treatment or prevention of onychomycosis.

Effects of the Invention

According to the present invention, a pharmaceutical composition for external use to be stored in a state in which luliconazole or the like is dissolved and prevented from a decrease in optical purity thereof can be provided.

BEST MODE FOR CARRYING OUT THE INVENTION (1) Luliconazole and/or a Salt Thereof as Essential Components of a Pharmaceutical Composition for External Use (Hereinafter, Referred to as Pharmaceutical Composition of the Present Invention)

The pharmaceutical composition for external use of the present invention contains as essential components luliconazole and/or a salt thereof. The above-mentioned luliconazole is represented by the above-mentioned structural formula (1). The above-mentioned luliconazole is a known compound represented by (−)-(E)-[(4R)-(2,4-dichlorophenyl)-1,3-dithiolan-2-iliden]-1-imidazolyl acetonitrile. Its manufacturing method and the antifungal properties are already known in the art. JP 62-93227 A (Patent Document 7 above) can be used as reference.

In addition, "salt thereof" is not specifically limited as far as it is physiologically acceptable. Preferable examples thereof include: mineral acid salts such as hydrochloride, nitrate, sulfate, and phosphate; organic acid salts such as citrate, oxalate, lactate, and acetate; and sulfuric acid-containing salts such as mesilate and tosilate. In terms of safety and solubility, hydrochloride is more preferable.

In the pharmaceutical composition for external use of the present invention, the content of luliconazole or the like is preferably 0.1 to 30% by mass, more preferably 0.5 to 15% by mass in total with respect to the total amount of the pharmaceutical composition. The content of luliconazole or the like can be determined based on its solubility and formulation characteristics.

(2) Essential Component of Pharmaceutical Composition for External Use of the Present Invention: N-methyl-2-pyrrolidone, Propylene Carbonate, or Crotamiton The pharmaceutical composition for external use of the present invention contains one or two or more organic solvents selected from N-methyl-2-pyrrolidone, propylene carbonate, and crotamiton as an essential component. Obviously, for the organic solvent, there may be used a single kind thereof or a combination of two or more kinds thereof. In the pharmaceutical composition of the present invention, among the above organic solvents, it is preferable to contain at least N-methyl-2-pyrrolidone, particularly both N-methyl-2-pyrrolidone and propylene carbonate. The organic solvent of such a preferable aspect is excellent not only in action of dissolving luliconazole or a salt thereof but also in action of suppressing, in a dissolved state, a decrease in optical purity. For exerting such an action sufficiently, the total content of such a solvent is preferably 0.1 to 40% by mass, more preferably 1 to 10% by mass with respect to the total amount of the pharmaceutical composition.

(3) Pharmaceutical Composition for External Use of the Present Invention

The pharmaceutical composition for external use of the present invention can contain any of components commonly used in pharmaceutical compositions in addition to those described above, as far as it does not impair the effects of the present invention.

Preferable examples of such components include: hydrocarbons such as vaseline and microcrystalline wax; esters such as jojoba oil and cetaceum; triglycerides such as beef tallow and olive oil; higher alcohols such as cetanol and oleyl alcohol; fatty acids such as stearic acid and oleic acid; alcohols such as ethanol and isopropanol; polyalcohols such as glycerin and 1,3-butanediol; water; non-ionic surfactants; anionic surfactants; cationic surfactants; amphoteric surfactants; thickeners such as polyvinyl pyrrolidone and carbopol; preservatives; UV absorbers; antioxidants; pigments; and powders. Those optional components and the above-mentioned component are treated by common procedures, whereby a pharmaceutical composition for external use of the present invention can be produced. The pharmaceutical composition for external use of the present invention is not specifically limited as far as it is formulated into any of forms used for pharmaceutical composition for external uses, and preferable examples thereof include lotions, emulsions, gelatinizing agents, cream pharmaceuticals, aerosols, nail enamel agents, and hide gel patches. Of those, the lotions are most preferable. For stabilizing the clarity and color of solution such as luliconazole, 50 to 90% by mass of ethanol is most preferably contained.

The pharmaceutical composition for external use of the present invention is preferably used for treating mycotic diseases or preventing progression of the diseases by using characteristics of luliconazole or the like. The mycotic diseases include: foot trichophytosis such as athlete's foot; trichophytosis corporis such as candida and pityriasis versicolor; and trichophytosis on a hard keratin portion, such as onychomycosis. Because of remarkable effects, it is particularly preferable to use the pharmaceutical composition for external use of the present invention for treating the hard keratin portion, such as onychomycosis. In particular, the pharmaceutical composition for external use of the present invention exerts preferable effects on the nail and such an effect is also exerted on typical dermatomycosis. Therefore, the application of a pharmaceutical composition for external use against dermatomycosis, which satisfies the configuration of the present invention, is also within the technical scope of the present invention. Examples of such dermatomycosis include trichophytosis such as foot trichophytosis, particularly horny-outgrowing type hyperkeratotic trichophytosis which appears on heels or the like. The present invention has a significant effect on the horny-outgrowing type hyperkeratotic trichophytosis, on which the conventional agents hardly exert their effects, among the above-mentioned dermatomycosis, which is preferable.

With regard to its use, for example, the pharmaceutical composition is applied on a diseased portion one or several times a day and the treatment is preferably carried out day after day. In particular, for onychomycosis, luliconazole or the like, which is an effective component in an amount that cannot be attained by normal formulation, can be transferred into the nail. Therefore, onychomycosis can be treated only by the external application without having to drink an antifungal agent over a long period of time. In addition, recurrence and reinfection have been a major problem for onychomycosis. However, the recurrence and reinfection can be prevented by application of the pharmaceutical composition for external use of the present invention for 1 to 2 weeks after abatement of the symptom. Therefore, the pharmaceutical composition for external use of the present invention exerts preventive efficacy in this aspect.

EXAMPLES

Hereinafter, the present invention will be described in more detail with reference to examples. However, the present invention is not limited to those examples.

Examples 1 to 6 and Comparative Examples 1 to 4

According to the formulation shown in Table 1, Pharmaceutical Preparations 1 to 6 each containing the pharmaceutical composition for external use of the present invention were prepared. That is, formulation components were stirred at room temperature and components for pharmaceutical preparation were then dissolved, thereby obtaining a pharmaceutical preparation of a clear lotion dosage form. Here, the value represents "% by mass". Likewise, according to Table 2, Comparative Pharmaceutical Preparations 1 to 4 for the respective comparative examples were also prepared.

TABLE 1

| | Pharmaceutical Preparations | | | | | |
|---|---|---|---|---|---|---|
| | 1 | 2 | 3 | 4 | 5 | 6 |
| Luliconazole | 1 | 1 | 1 | 1 | 1 | 1 |
| N-methyl-2-pyrrolidone | 5 | | | 8 | 5 | 8 |
| Propylene carbonate | | 5 | | 10 | | |
| Crotamiton | | | 5 | | | |
| Squalane | | | | | | 5 |
| 1,3-butylene glycol | | | | | 20 | 25 |
| Concentrated glycerin | | | | | | 3 |
| Cetanol | | | | | | 0.75 |
| POE (10) hydrogenated castor oil | | | | | | 1 |
| POE (10) lauric acid | | | | | | 0.25 |
| Stearic acid monoglyceride | | | | | | 0.25 |
| Water | | | | | 10 | 55.75 |
| Ethanol | 94 | 94 | 94 | 81 | 64 | |

TABLE 2

| | Comparative Pharmaceutical Preparations | | | |
|---|---|---|---|---|
| | 1 | 2 | 3 | 4 |
| Luliconazole | 1 | 1 | 1 | 1 |
| Dimethyl sulfoxide | 5 | | | |
| Methyl ethyl ketone | | 5 | | |
| Ethyl acetate | | | 5 | |
| Ethanol | 94 | 94 | 94 | 99 |

Experimental Examples

Pharmaceutical Preparations 1 to 6 and Comparative Pharmaceutical Preparations 1 to 4 as described above were subjected to two-week storage experiments under conditions of 40° C. and 60° C. Immediately before and after the storage experiment, the amount of an SE body ((S)-(+) isomer) produced, which is an enantiomer of luliconazole, was measured by HPLC and expressed in area percentage to investigate the stability thereof. The results are shown in Table 3. Consequently, it can be recognized that any of the pharmaceutical composition for external uses of the present invention is stored in a state where a decrease in optical purity is suppressed.

<HPLC Conditions>
  Instrument used: LC-97 system (Shimadzu Corporation)
  Column: CHIRALPACK AD-H 4.6 mm×250 mm
  Column temperature: 40° C.
  Mobile phase: Water:acetonitrile=90:11 to 60:40 (30-minute gradient condition)
  Flow rate: 0.8 ml/min
  Detection: UV (300 nm in wavelength)
  Quantitative assay: an area-percentage method using an absolute working curve

TABLE 3

| | Stability (Increased amount of SE isomer) | | |
|---|---|---|---|
| | At start | 40°, 2 Week | 60°, 2 Week |
| Pharmaceutical preparation 1 | 0.16 | 1.11 | 3.03 |
| Pharmaceutical preparation 2 | 0.21 | 2.13 | 14.89 |
| Pharmaceutical preparation 3 | 0.15 | 0.55 | 5.79 |
| Pharmaceutical preparation 4 | 0.14 | 0.18 | Not detected |

TABLE 3-continued

| | Stability (Increased amount of SE isomer) | | |
|---|---|---|---|
| | At start | 40°, 2 Week | 60°, 2 Week |
| Pharmaceutical preparation 5 | 0.44 | 0.52 | Not detected |
| Pharmaceutical preparation 6 | 0.32 | 0.43 | Not detected |
| Comparative preparation 1 | 0.20 | 5.09 | 23.01 |
| Comparative preparation 2 | 0.23 | 8.69 | 32.73 |
| Comparative preparation 3 | 0.19 | 3.30 | 31.15 |
| Comparative preparation 4 | 0.16 | 8.70 | 41.68 |

INDUSTRIAL APPLICABILITY

According to the present invention, a pharmaceutical composition for external use to be stored in a state where luliconazole or the like is dissolved and a decrease in optical purity thereof is suppressed can be provided.

What is claimed is:

1. A pharmaceutical composition for external use, comprising:
   i) R-luliconazole represented by the following structural formula (1) and/or a salt thereof; and
   ii) propylene carbonate at a concentration of 0.1 to 40% by mass
   (−)-(E)-[(4R)-(2,4-dichlorophenyl)-1,3-dithiolan-2-iliden]-1-imidazolyla cetonitrile Structural formula (1)

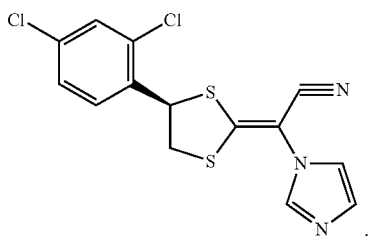

2. A pharmaceutical composition according to claim 1, wherein the composition comprises propylene carbonate in an amount of 1 to 10% by mass of the composition.

3. A pharmaceutical composition according to claim 1, wherein the composition comprises (R)-luliconazole in an amount of 0.5 to 15% by mass of the composition.

4. A pharmaceutical composition according to claim 1, wherein the composition further comprises ethanol.

5. A pharmaceutical composition according to claim 4, wherein the composition comprises ethanol in amount of 50 to 90% by mass of the composition.

6. A method of treating mycotic disease comprising externally administering the composition of claim 1 to an individual in need of treatment.

7. A method according to claim 6, wherein the mycotic disease is foot trichophytosis, trichophytosis corporis or trichophytosis on a hard keratin portion.

8. A method according to claim 6, wherein the mycotic disease is athlete's foot.

9. A method according to claim 6, wherein the mycotic disease is onychomycosis.

10. A method according to claim 6, wherein the mycotic disease is a mycotic disease of a nail.

11. A method according to claim 6, wherein the mycotic disease is dermatomycosis.

12. A pharmaceutical composition according to claim 2, wherein the composition comprises (R)-luliconazole in an amount of 0.5 to 15% by mass of the composition.

13. A pharmaceutical composition according to claim 2, wherein the composition further comprises ethanol.

14. A pharmaceutical composition according to claim 13, wherein the composition comprises ethanol in amount of 50 to 90% by mass of the composition.

15. A pharmaceutical composition according to claim 3, wherein the composition further comprises ethanol.

16. A pharmaceutical composition according to claim 15, wherein the composition comprises ethanol in amount of 50 to 90% by mass of the composition.

17. A pharmaceutical composition according to claim 12, wherein the composition further comprises ethanol.

18. A pharmaceutical composition according to claim 17, wherein the composition comprises ethanol in amount of 50 to 90% by mass of the composition.

19. A pharmaceutical composition for external use, consisting essentially of:
   i) (−)-(E)-[(4R)-(2,4-dichlorophenyl)-1,3-dithiolan-2-iliden]-1-imidazolyl acetonitrile and/or a salt thereof; and
   ii) propylene carbonate at a concentration of 0.1 to 40% by mass.

20. The pharmaceutical composition of any of claim 1, 3, 4, 12 or 14, wherein the pharmaceutical composition is formulated as a lotion.

* * * * *

UNITED STATES PATENT AND TRADEMARK OFFICE
CERTIFICATE OF CORRECTION

PATENT NO. : 8,349,882 B2
APPLICATION NO. : 12/281967
DATED : January 8, 2013
INVENTOR(S) : Kobayashi et al.

Page 1 of 1

It is certified that error appears in the above-identified patent and that said Letters Patent is hereby corrected as shown below:

On the Title Page

In column 2 (page 1 item 56) at line 31, Under Other Publications, change "WO/2007077806" to --WO 2007/077806--.

In the Specification

In column 6 at line 47 (approx.), Change "CHIRALPACK" to --CHIRALPAK--.

In the Claims

In column 7 at line 33, In Claim 1, change "imidazolyla cetonitrile" to --imidazolyl acetonitrile--.

In column 8 at line 47 (approx.), In Claim 20, change "1, 3," to --1, 2, 3,--.

Signed and Sealed this
Sixth Day of August, 2013

Teresa Stanek Rea
*Acting Director of the United States Patent and Trademark Office*